US008093296B2

(12) United States Patent
Davis

(10) Patent No.: US 8,093,296 B2
(45) Date of Patent: *Jan. 10, 2012

(54) METHODS FOR CONCOMITANT ADMINISTRATION OF COLCHICINE AND MACROLIDE ANTIBIOTICS

(75) Inventor: Matthew W. Davis, Erwinna, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/090,697

(22) Filed: Apr. 20, 2011

(65) Prior Publication Data

US 2011/0190396 A1 Aug. 4, 2011

Related U.S. Application Data

(63) Continuation of application No. 12/576,355, filed on Oct. 9, 2009, which is a continuation-in-part of application No. 12/327,258, filed on Dec. 3, 2008, now Pat. No. 7,619,004, said application No. 12/576,355 is a continuation-in-part of application No. 12/368,700, filed on Feb. 10, 2009, now Pat. No. 7,601,758.

(60) Provisional application No. 61/190,053, filed on Oct. 15, 2008.

(51) Int. Cl.
| | |
|---|---|
| A01N 37/18 | (2006.01) |
| A61K 31/16 | (2006.01) |
| C07C 233/00 | (2006.01) |
| C07C 235/00 | (2006.01) |
| C07C 237/00 | (2006.01) |
| C07C 239/00 | (2006.01) |
| C07C 211/00 | (2006.01) |
| C07C 205/00 | (2006.01) |
| C07C 207/00 | (2006.01) |

(52) U.S. Cl. ........ 514/629; 564/123; 564/308; 564/427; 568/306

(58) Field of Classification Search .................. 514/629; 564/123, 308, 427; 568/306
See application file for complete search history.

(56) References Cited

U.S. PATENT DOCUMENTS

| | | | |
|---|---|---|---|
| 5,758,095 | A | 5/1998 | Albaum et al. |
| 5,833,599 | A | 11/1998 | Schrier et al. |
| 5,845,255 | A | 12/1998 | Mayaud |
| 5,914,332 | A | 6/1999 | Sham et al. |
| 6,014,631 | A | 1/2000 | Teagarden et al. |
| 6,037,157 | A | 3/2000 | Norbeck et al. |
| 6,067,524 | A | 5/2000 | Byerly et al. |
| 6,112,182 | A | 8/2000 | Akers et al. |
| 6,317,719 | B1 | 11/2001 | Schrier et al. |
| 6,356,873 | B1 | 3/2002 | Teagarden et al. |
| 7,072,840 | B1 | 7/2006 | Mayaud |
| 7,601,758 | B1 | 10/2009 | Davis |
| 7,619,004 | B1 | 11/2009 | Davis |
| 7,820,681 | B1 * | 10/2010 | Davis .................. 514/263.31 |
| 7,906,519 | B2 * | 3/2011 | Davis .................. 514/263.31 |
| 7,915,269 | B2 * | 3/2011 | Davis .................. 514/263.31 |
| 7,935,731 | B2 | 5/2011 | Davis |

OTHER PUBLICATIONS

Wang et al. 2001, "HMG-CoA reductase inhibitors (Statins) characterized as direct inhibitors of P-glycoprotein." Pharmaceutical Research, vol. 18, No. 6, pp. 800-806.*
U.S. Appl. No. 12/687,406, filed Jan. 2010, Davis, Matthew W.*
U.S. Appl. No. 12/407,980, filed Mar. 2009, Davis, Matthew W.*
U.S. Appl. No. 12/688,038, filed Jan. 2010, Davis, Matthew W.*
U.S. Appl. No. 12/576,355, filed Oct. 2009, Davis, Matthew W.*
U.S. Appl. No. 12/909,171, filed Oct. 2010, Davis, Matthew W.*
U.S. Appl. No. 12/545,120, filed Aug. 2009, Davis, Matthew W.*
U.S. Appl. No. 13/092,459, filed Apr. 2011, Davis, Matthew W.*
U.S. Appl. No. 13/109,034, filed May 2011, Davis, Matthew W.*
U.S. Appl. No. 13/110,087, filed May 2011 Davis, Matthew W.*
Cheng, et al.; "Two Probable Cases of Serious Drug Interaction Between Clarithromycin and Colchicine"; Southern Medical Journal; p. 811, (2005).
Horn, et al.; "Life-threatening Colchicine Drug Interactions"; Pharmacy Times; p. 111; (2006).
Hung et al.; "Fatal Interaction Between Clarithromycin and Colchicine in Patients with Renal Insufficiency: A Retrospective Study"; Clinical Infectious Diseases; 41; pp. 291-300; (2005).
Leikin ete al.; "Colchicine"; Poisoning and Toxicology Handbook, Fourth Edition; p. 216; (2007).
Perez-Ruiz, et al.; "Optimisation of the Treatment of Acute Gout"; BioDrugs; 13; pp. 415-423; (2000).
Rollot, et al.; "Acute Colchicine Intoxication During Clarithromycin Administration"; The Annals of Pharmacotherapy; 38; pp. 2074-2077; (2004).
Terkeltaub, Robert A.; "Gout"; The New England Journal of Medicine; 349; pp. 1647-1655; (2003).
Terkeltaub, et al.; "Comparison of Low-Dose vs High-Dose Oral Colchicine Regimens in Patients with Gout Flares"; Prescentation at the American College of Rheumatology Scientific Meeting; San Francisco, CA; Oct. 24-29; (2008).
Terkeltaub, et al.; "The Clinical Relevance of P-gp and CYP 3A4 on Colchicine Metabolism and Elimination"; Presentation at the American College of Rheumatology Scientific Meeting; San Francisco, CA; Oct. 24-29; (2008b).
Van Der Velden, et al.; "Colchicine-Induced Neuromyopathy in a Patient with Chronic Renal Failure: The Role of Clarithromycin"; Netherlands Journal of Medicine; 66; pp. 204-206; (2008).
Waknine, Yael; "FDA Safety Changes: Dexedrine and Biaxin CME/CE"; Medscape Medical News; http://bcbsma.medscape.com/viewarticle/54411; 5 pages; (2006).
Clarithromycin Tablets, USP; Clarithromycin for Oral Suspension, USP, BIAXIN XL Filmtab; Abbott Laboratories; 07E-010-U780-4 Master; 26 pages; Reference 03-5569-R3 Revised Mar. 2007.
Concomitant Drugs (Wikidpedia document) http://en.wikipedia.org/wiki/Concomitant_drugs; printed May 28, 2009, 2 pages.

(Continued)

Primary Examiner — Sreeni Padmanabhan
Assistant Examiner — Kara R McMillian
(74) Attorney, Agent, or Firm — Cantor Colburn LLP

(57) ABSTRACT

Methods for concomitant administration of colchicine together with one or more macrolide antibiotics, e.g., clarithromycin, are disclosed. Such methods reduce the dangers commonly associated with such concomitant administration and provide additional benefits.

3 Claims, 2 Drawing Sheets

OTHER PUBLICATIONS

Drugs.com; "Colchicine Dosage" (available on line http://www.drugs.com/dosage/colchicine.html); 6 pages; accessed Sep. 20, 2010.

Krishnan et al.; "Gout in Ambulatory Care Settings in the United States"; Journal of Rheumatology; 35; pp. 498-501; (2008).

Lacy et al.; Lexi-Comp's Clinical Reference Library, Drug Information Handbook, 7th Ed., pp. 108-109 and 292-293; (1999-2000).

Morris, et al.; "Lesson of the Week—Colchicine in Acute Gout"; BMJ; 327; pp. 1275-1276; (2003).

U.S. Appl. No. 12/327,258 Final Office Action dated Apr. 16, 2009; 24 pages.

U.S. Appl. No. 12/327,258 Non-final Office Action dated Feb. 13, 2009; 20 pages.

U.S. Appl. No. 12/327,258 Final Office Action dated Jul. 24, 2009; 22 pages.

U.S. Appl. No. 12/327,258 Non-final Office Action dated Jun. 4, 2009; 33 pages.

U.S. Appl. No. 12/368,700 Non-final Office Action dated Apr. 27, 2009; 77 pages.

Ogbru, Omudhome (www.medicinenet.com/colchicine/article.htm; 2 pages; (2008).

Rango; "Management of Goup with Colchicine"; http://www.theberries.ca/Archives/colchicine.html; 4 pages; available on line as of Jul. 5, 2003).

Rx-s.net/weblog/more/colchicine-indications-and-dosage/;

"Colchicine Indications and Dosage"; 5 pages; last revised Aug. 2, 2005.

Akdag et al.; "Acute Colchicine Intoxication During Clarithromycin Administration in Patients With Chronic Renal Failure"; J. Nephrol; 19; pp. 515-517; (2006).

Caraco, et al.; Acute Colchicine Intoxication—Possible Role of Erythromycin Administration; Journal of Rheumatology; 19:3; pp. 494-496; (1992).

"Colchicine: Serious Interactions"; prepared by editorial staff; Translated from Rev. Prescrire; 28(294); pp. 267-270); (2008).

Dogukan et al.; "Acute Fatal Colchicine Intoxication in a Patient on Continuous Ambulatory Peritoneal Dialysis (CAPD). Possible Role of Clarithromycin Administration"; Clinical Nephrology; 55(2); pp. 181-182; (2001).

Achtert et al.; "Pharmacokinetics / bioavailability of colchicine in healthy male volunteers"; European Journal of Drug Metabolism and Pharmacokinetics; 14(4); pp. 317-322; (1989).

Ahern et al., "Does Colchicine Work? The results of the first controlled study in acute gout"; Aust NZ J Med 1987; 17: 301-304.

Dahan et al., "Grapefruit Juice and its Constituents Augment Colchicine Intestinal Absorption: Potential Hazardous Interaction and the Role of P-Glycoprotein", Pharm Res. 2009; 26(4); 883-92; Epub Dec. 2, 2008.

Goldbart, et al.; Near Fatal Acute Colchicine Intoxication in a Child. A Case Report; Eur J Pediatr; 159; pp. 895-897; (2000).

"Guidance for Industry—In Vivo Drug Metabolism/Drug Interaction Studies—Study Design, Data Analysis, and Recommendations for Dosing and Labeling"; 19 pages; USDA; Nov. 1999.

"Risk of Drug Interactions Involving Herbval and Citrus Products"; Health Canada International Symposium on Drug, Food and Natural Health Product Interactions; Gatineau, Quebec, 61 pages; powerpoint presentation; Feb. 9, 2006.

Sabouraud, et al.; "Pharmacokinetics of Colchicine: A Review of Experimental and Clinical Data"; 2 Gastroenterol (Suppl. 1); 30; pp. 35-39p (1992).

Brooks; "Rheumatic Disorders" Chapter 25 of Avery's Drug Therapy, Pub. 1997 by Adis International, pp. 1113-1161.

Terkeltaub, Robert A.; "Colchicine Update: 2008"; Seminars in Arthritis and Rheumatism; VA Medical Center, University of California San Diego; (2009), 38(6), 411-419.

\* cited by examiner

METHODS FOR CONCOMITANT ADMINISTRATION OF COLCHICINE AND MACROLIDE ANTIBIOTICS

CROSS REFERENCE TO RELATED APPLICATIONS

This application is a continuation of U.S. application Ser. No. 12/576,355 filed Oct. 9, 2009, which is a continuation-in-part of U.S. patent application Ser. No. 12/327,258 filed on Dec. 3, 2008, now U.S. Pat. No. 7,619,004, issued Nov. 17, 2009, and a continuation of part of U.S. application Ser. No. 12/368,700 filed on Feb. 10, 2009, now U.S. Pat. No. 7,601,758, issued Oct. 13, 2009, all of which claim the benefit of Provisional Patent Application Ser. No. 61/190,053, filed Oct. 15, 2008, and all of which are incorporated herein in their entirety.

BACKGROUND

This application relates to methods allowing for the co-administration of colchicine together with one or more macrolide antibiotics for therapeutic purposes with less danger than is associated with prior methods of administration.

Colchicine:

Colchicine, chemical name (−)-N-[(7S,12aS)-1,2,3,10-tetramethoxy-9-oxo-5,6,7,9-tetrahydrobenzo[a]heptalen-7-yl]-acetamide, is a pale yellow powder soluble in water in 1:25 dilution.

Colchicine is an alkaloid found in extracts of *Colchicum autumnale, Gloriosa superba*, and other plants. Among its many biological activities, colchicine blocks microtubule polymerization and arrests cell division. It has adversely affected spermatogenesis in humans and in some animal species under certain conditions.

Colchicine is a microtubule-disrupting agent used in the treatment of gout and other conditions that may be treated, relieved or prevented with anti-inflammatory treatment. Colchicine impairs the motility of granulocytes and can prevent the inflammatory phenomena that initiate an attack (or flare) of gout. Colchicine also inhibits mitosis, thus affecting cells with high turnover such as those in the gastrointestinal tract and bone marrow; therefore, the primary adverse side effects include gastrointestinal upset such as diarrhea and nausea. More serious side effects include morbid complications such as myopathy, neuropathy, bone marrow suppression and drug-induced cytopenia. Particular expressions of these morbid complications may include neuromuscular toxicity with paresthesias, pancytopenia, and seizures.

Colchicine has a low therapeutic index. The margin between an effective dose and a toxic dose of colchicine is much narrower than that of most other widely used drugs. Consequently, actions that result in increased colchicine levels in patients receiving colchicine therapy are particularly dangerous. Co-administration of colchicine to patients along with certain other drugs can have the effect of increasing colchicine levels. Such drug-drug interactions with colchicine have been reported to result in serious morbid complications and, in some cases, death.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10 to 20% eliminated unchanged in the urine.

Gout:

Gout (or gouty arthritis) is a disease caused by a build up of uric acid. Such a build up is typically due to an overproduction of uric acid or to a reduced ability of the kidney to excrete uric acid. Gout is more common in certain groups of patients, including adult males, postmenopausal women, and hypertensives. Heavy alcohol use, diabetes, obesity, sickle cell anemia, and kidney disease also increase the risk of developing gout. The condition may also develop in people who take drugs that interfere with uric acid excretion.

In gout, crystals of monosodium urate (a salt of uric acid) are deposited in joints, e.g., on articular cartilage, as well as in and on tendons and surrounding tissues. These deposits correlate with elevated concentrations of uric acid in the blood stream and are believed to provoke the painful inflammatory reaction that occurs in affected tissues. Gout is characterized by excruciating, sudden, unexpected, burning pain, as well as by swelling, redness, warmness, and stiffness in the affected joint. Low-grade fever may also be present. The patient usually suffers from two sources of pain. The patient experiences intense pain whenever an affected joint is flexed. The inflammation of the tissues around the joint also causes the skin to be swollen, tender and sore if it is even slightly touched. For example, a blanket or even the lightest sheet draping over the affected area could cause extreme pain.

A gout flare is a sudden attack of pain in affected joints, especially in the lower extremities, and most commonly in the big toe. In afflicted individuals, the frequency of gout flares typically increases over time. In this fashion, gout progresses from acute gout to chronic gout, which involves repeated episodes of joint pain.

In acute gout flares, symptoms develop suddenly and usually involve only one or a few joints. The big toe, knee, or ankle joints are most often affected. The pain frequently starts during the night and is often described as throbbing, crushing, or excruciating. The joint appears infected, with signs of warmth, redness, and tenderness. Gout flares appear substantially more frequently with more intensive urate-lowering regimens and are a common consequence of therapy with allopurinol. Two randomized clinical trials assessed the efficacy of colchicine 0.6 mg twice a day for the prophylaxis of gout flares in patients with gout initiating treatment with urate lowering therapy. In both trials, treatment with colchicine decreased the frequency of gout flares. Flares of painful joints may go away in several days, but may return from time to time. Subsequent flares usually last longer. Acute gout may progress to chronic gout flares, or may resolve without further attacks.

The chronic appearance of several attacks of gout yearly can lead to joint deformity and limited joint motion. Nodular uric acid deposits, called tophi, may eventually develop in cartilage tissue, tendons, and soft tissues. These tophi are a hallmark of chronic gout, which usually develop only after a patient has suffered from the disease for many years. Deposits of monosodium urate can also occur in the kidneys of gout sufferers, potentially leading to chronic kidney failure.

Use of Colchicine to Treat Gout:

Colchicine can reduce pain in attacks of acute gout flares and also can be used beneficially for treating adults for prophylaxis of gout flares. Although its exact mode of action in the relief of gout is not completely understood, colchicine is known to decrease the inflammatory response to urate crystal deposition by inhibiting migration of leukocytes, to interfere with urate deposition by decreasing lactic acid production by leukocytes, to interfere with kinin formation and to diminish phagocytosis and subsequent inflammatory responses.

The anti-inflammatory effect of colchicine is relatively selective for gouty arthritis. However, other types of arthritis occasionally respond. It is neither an analgesic nor a uricosuric and will not prevent progression of acute gout to chronic gout. It does have a prophylactic, suppressive effect that helps to reduce the incidence of acute attacks as well as to relieve the residual pain and mild discomfort that patients with gout occasionally experience between attacks.

Macrolide Antibiotics:

Macrolide compounds are natural products and natural product derivatives characterized by the presence of a macrocyclic (large) lactone ring known as a macrolide ring. The macrolide antibiotics are important therapeutic agents. Commercially available macrolide antibiotics include azithromycin, clarithromycin, dirithromycin, erythromycin, and roxithromycin.

Clarithromycin is a semi-synthetic macrolide antibiotic with in vitro activity against a variety of aerobic and anaerobic gram-positive and gram-negative microorganisms, as well as most *Mycobacterium avium* complex (MAC) microorganisms. The drug is believed to exert its antibacterial action by binding to 50S ribosomal subunits in susceptible microorganisms, resulting in inhibition of protein synthesis.

Clarithromycin is indicated in the treatment of mild to moderate infections in adults and children caused by susceptible strains of microorganisms, such as *Legionella pneumophila. Haemophilus influenzae, Streptococcus pneumoniae* and *Neisseria gonorrhoeae*. Clarithromycin is also used to treat pharyngitis (tonsillitis), sinusitis, bronchitis, community-acquired pneumonia, uncomplicated skin infections, and disseminated mycobacterial infections. The usual adult dose is 250 or 500 mg every 12 hours (500 or 100 mg per day) for 7 to 14 days, taken without regard to food.

Clarithromycin is rapidly absorbed from the gastrointestinal tract following oral administration, with an absolute bioavailability of approximately 50%. Peak plasma concentrations with single doses are reached within 2 to 3 hours and steady-state plasma concentrations are reached within 3 to 4 days. Food slightly delays the onset of absorption and time to peak concentration and increases the peak concentration by about 24%, but does not affect the extent of exposure. Clarithromycin distributes readily into body tissues and fluids and is not highly bound to plasma proteins (65 to 75%).

Cytochrome p450 (CYP) Enzymes:

CYP enzymes are agents of drug metabolism that are found in the liver, the gastrointestinal tract and other locations in the body. CYP enzymes occur in a variety of closely related proteins referred to as isozymes. Some of these that have been identified as important in drug metabolism are CYP1A2, CYP2A6, CYP2B6, CYP2C8, CYP2C9, CYP2C19, CYP2D6, CYP2E1, CYP3A4, and CYP3A5. Different CYP isozymes may preferentially metabolize different drugs. For example, phenytoin and fosphenytoin have been reported to be preferentially metabolized by CYP2C9, CYP2C19, and CYP3A4, while CYP2D6 has been reported to be responsible for the metabolism of many psychotherapeutic agents, such as thioridazine.

CYP Isozymes and Drug-Drug Interactions:

Examples of CYP-mediated drug-drug interactions include those involving CYP1A2 and CYP2E1 isozymes, which have been reported to be involved in drug-drug interactions involving theophylline, and those involving CYP2C9, CYP1A2, and CYP2C19, which have been reported to be involved in drug-drug interactions involving warfarin.

The 3A family of CYP isozymes, particularly CYP3A4, is also known to be involved in many clinically significant drug-drug interactions, including those involving colchicine and macrolide antibiotics, as well as those involving non-sedating antihistamines and cisapride. CYP3A5 shares very similar protein structure, function and substrate specificity with CYP3A4. The CYP3A5*3 allele is a gene variant that does not express CYP3A5 enzyme. As a result of this genetic variation, about half of African-American subjects and 70-90% of Caucasian subjects do not express CYP3A5, while expression is more common in other ethnic groups.

While drugs are often targets of CYP-mediated metabolism, some may also alter the expression and activity of such enzymes, thus impacting the metabolism of other drugs.

Colchicine is both a target of and a modulator of CYP isozymes. The biotransformation of colchicine in human liver microsomes involves formation of 3-demethylchochicine and 2-demethylcolchicine. As shown by experiments using antibodies against CYP3A4 and experiments using chemical inhibition of CYP3A4, this transformation is correlated with (and thus apparently mediated by) CYP3A4 activity. CYP2A6, CYP2C9, CYP2C19, CYP2D6, and CYP2E1 do not appear to catalyze this biotransformation.

Studies on the effect of colchicine on expression of selected CYP isozymes in primary cultures of human hepatocytes have been reported. Dvorak et al. (Acta Univ. Palacki. Olomuc., Fac. Med. (2000) 143:47-50) provided preliminary data on the effect of colchicine and several of its derivatives on protein levels of CYP1A2, CYP2A6, CYP2C9/19, CYP2E1, and CYP3A4 as assessed by immunoblotting. Colchicine caused an increase in CYP2E1 protein levels and appeared to decrease protein levels of CYP1A2, CYP2C9/19, and CYP3A4, with 10 µM colchicine causing a greater reduction in each isozyme than 1 µM colchicine. The 3-demethylchochicine metabolite was reported to cause a decrease in protein for CYP1A2, CYP2C9/19, CYP2E1, and CYP3A4. The levels of CYP2A6 appeared unaffected by colchicine or any of the tested metabolites. In a more complete report on expression of CYP1A2, CYP2A6, CYP2C9, CYP2C19, CYP2E1, and CYP3A4, Dvorak et al. (Toxicology in Vitro (2002) 16:219-227) concluded that CYP1A2 protein content in 1 µM colchicine treated cells was not different from that in control cells, while the inducer TCDD increased the level of CYP1A2 protein by an average of three-fold. The levels of CYP2A6 protein were apparently unaffected by colchicine, while enzyme activities of CYP3A4 and CYP2C9 were significantly decreased by colchicine and activity of CYP2E1 was not affected. Northern blots showed that colchicine suppressed CYP2C9 mRNA levels by about 20% and did not alter CYP3A4 mRNA levels as compared to control cells. A subsequent study by Dvorak et al. (Mol. Pharmacol. (2003) 64:160-169) showed that colchicine decreased both basal and rifampicin-inducible and phenobarbital-inducible expression of CYP2B6, CYP2C8/9, and CYP3A4.

Like colchicine, clarithromycin is a target of metabolism by CYP3A isozymes. In non-fasting healthy human subjects, the elimination half-life of clarithromycin is about 3 to 4 hours with 250 mg administered every 12 hours, but increases to 5 to 7 hours with 500 mg administered every 8 to 12 hours. Approximately 20% and 30% of the dose, respectively, is excreted as unchanged drug in urine following oral administration of 250 and 500 mg clarithromycin given every 12 hours. Approximately 10 to 15% of the dose is excreted in urine as 14-hydroxyclarithromycin, an active metabolite of clarithromycin with substantial antibacterial activity. About 40% of an oral clarithromycin dose is excreted in feces.

Clarithromycin is also a potent inhibitor of CYP3A isozymes, as are other macrolide antibiotics. This inhibition is not rapidly reversible. Due to the limited reversibility of the inhibition of CYP3A isozymes by clarithromycin, CYP3A activity may not return to normal after a course of treatment with clarithromycin until the body produces adequate amounts of CYP3A isozymes to replace those irreversibly inhibited by the clarithromycin. Thus, it may take one to two weeks for CYP3A metabolic activity to return to normal following treatment with clarithromycin or other macrolide antibiotics.

P-glycoprotein (Pgp) is an ATP-dependent cell surface transporter molecule. Pgp actively pumps certain compounds, notably including drugs such as colchicine, out of cells. Pgp is encoded by the Adenosine triphosphate-binding cassette subfamily B member 1 (ABCB1) gene, also referred to as the multiple drug resistance 1 gene (MDR1).

Clarithromycin is an inhibitor of Pgp, as are other macrolide antibiotics. In vitro, agents that inhibit CYP 3A4 typically also inhibit Pgp, and the magnitude of Pgp inhibition in vitro generally trends proportionally with magnitude of CYP 3A4 inhibition. However, equipotent CYP 3A4 inhibitors can exhibit different degrees of Pgp inhibition.

Thus clarithromycin and other macrolide antibiotics, in addition to inhibiting the metabolic breakdown of colchicine by inhibiting CYP 3A4 isozymes, can block a mechanism by which colchicine is pumped out of cells. Both the inhibition of colchicine breakdown by CYP 3A4 and the inhibition of the pumping of colchicine out of cells by Pgp have the effect of increasing the intracellular levels of colchicine.

Since colchicine acts intracellularly, the combined effects of CYP 3A4 inhibition and Pgp inhibition by clarithromycin (and related macrolide antibiotics) can cause colchicine toxicity in patients taking what would be a safe dose of colchicine in the absence of concomitant macrolide antibiotic administration.

Drug-drug interactions, such as the enhancement of colchicine toxicity by macrolide antibiotics, present a health risk to patients and a medical challenge for all medical care workers. Various studies of adverse reactions from exposure to multiple drugs have found that 6.5-23% of the adverse reactions result from drug-drug interactions. Unfortunately, each year a number of deaths occur as the direct result of patients adding a concomitant prescription pharmaceutical product to their existing medication regimen.

With regard to co-administration of colchicine with clarithromycin and other macrolide antibiotics, warnings have recently been published urging caution, or arguing that the two drugs should not be co-administered. For example, on Jul. 5, 2006 the US Food and Drug Administration (the FDA) approved safety labeling changes for clarithromycin tablets, extended-release tablets, and oral suspension to warn of the risk for increased exposure to colchicine in patients receiving both drugs. The Warnings section of the prescribing information for clarithromycin now includes the following statement: "There have been post-marketing reports of colchicine toxicity with concomitant use of clarithromycin and colchicine, especially in the elderly, some of which occurred in patients with renal insufficiency. Deaths have been reported in some such patients." In addition, the following was added to the Precautions section of the prescribing information: "[c]olchicine is a substrate for both CYP3A and the efflux transporter, P-glycoprotein (Pgp). Clarithromycin and other macrolides are known to inhibit CYP3A and Pgp. When clarithromycin and colchicine are administered together, inhibition of Pgp and/or CYP3A by clarithromycin may lead to increased exposure to colchicine. Patients should be monitored for clinical symptoms of colchicine toxicity."

A 2006 report entitled "Life-threatening Colchicine Drug Interactions" cautioned that "[c]olchicine should not be used with clarithromycin or erythromycin, and given the potential for fatal outcomes, it would be prudent to avoid all PGP inhibitors with colchicine" (Horn, J. R. and Hansten, P. D., Pharmacy Times, May 2006, p. 111).

More recently, a publication in May, 2008 ended with the conclusion that "[t]he combined prescription of clarithromycin or other CYP3A4 inhibitors and colchicine should be avoided." Van der Velden, et al., (Neth. J. Med. 2008 May; 66(5):204-6).

There accordingly remains a need in the art for improved methods for administering colchicine to patients who are concomitantly being treated with macrolide antibiotics so as to reduce the occurrence of dangerous colchicine toxicity. The present disclosure addresses this need and provides further advantages.

SUMMARY

Figure 1:
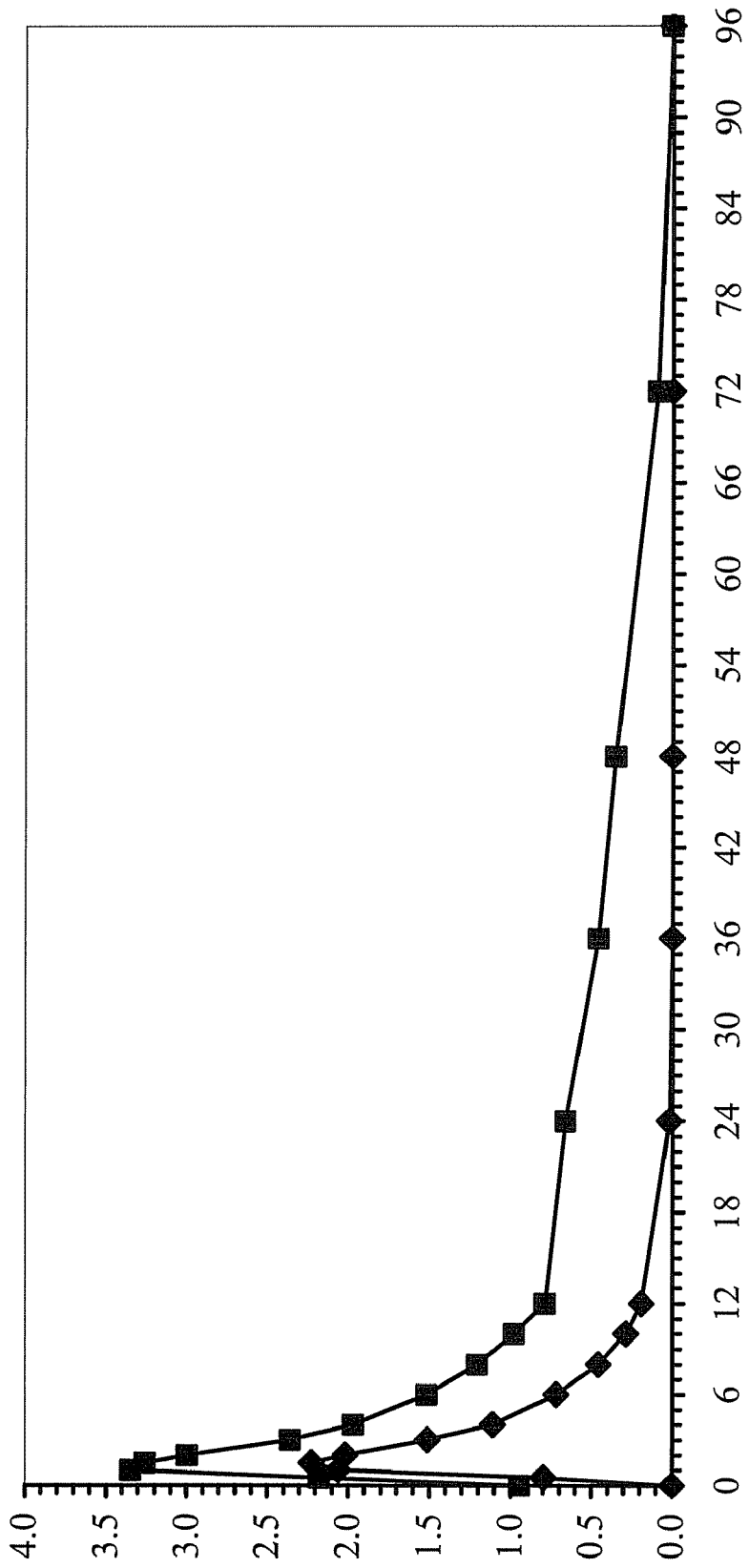
FIG. 1 shows mean colchicine plasma concentrations following administration of single and multiple oral doses of colchicine 0.6 mg in healthy adults, N=13, Y axis=colchicine concentration, ng/mL, X axis=time in hours, ♦=day 1, □=day 25. See Example 1.
Figure 2:
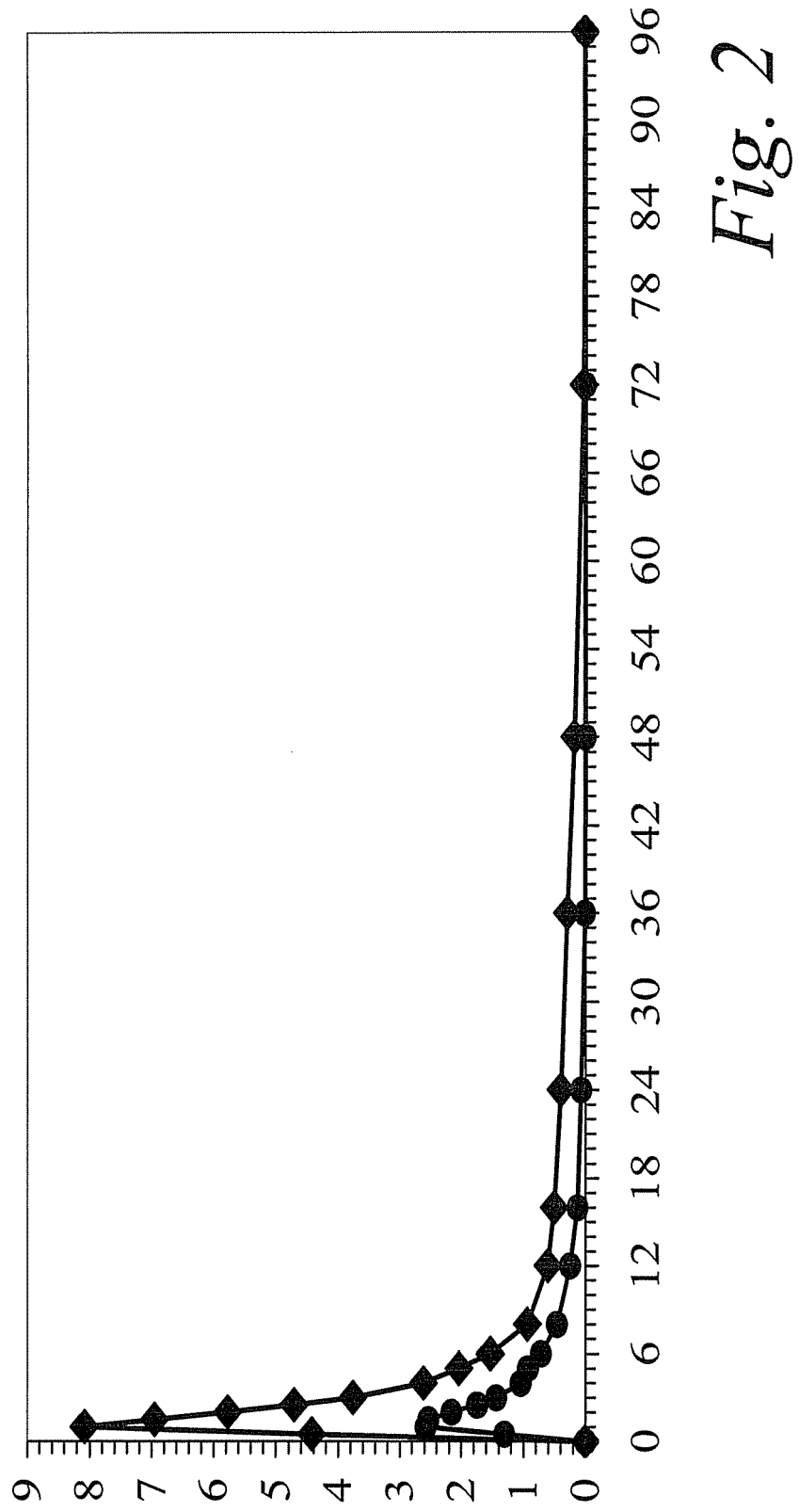
FIG. 2 shows a pharmacokinetic profile comparison of single-dose colchicine (0.6 mg, alone) and single-dose colchicine (0.6 mg) co-administered with steady-state clarithromycin in healthy adults, Y axis=colchicine concentration, ng/mL, X axis=time in hours, N=23, ●=day 1, ♦=day 29. See Example 2.

Disclosed herein are methods for more safely administering colchicine concomitantly with administration of macrolide antibiotics such as clarithromycin or erythromycin. It has now been discovered that certain reduced or limited colchicine dosages, when administered with concomitantly administered recommended dosage amounts of macrolide antibiotics, certain "colchicine plus macrolide" dosing regimens, achieve plasma colchicine levels that are therapeutically effective, but are not significantly higher, and therefore not significantly more toxic, than plasma levels achieved by administration of manufacturers' recommended colchicine dosage amounts in the absence of concomitant macrolide antibiotic administration. Thus, in spite of recent published warnings that the two should not be concomitantly administered, colchicine and macrolide antibiotics can be administered concomitantly without undue hazard when colchicine is administered as disclosed herein.

In one embodiment, colchicine treatment is administered to a patient in suffering from a condition treatable with colchicine, and the patient is concomitantly receiving administration of a macrolide antibiotic to treat an infection. The colchicine therapy may involve either palliative or prophylactic treatment, or both.

In one embodiment, colchicine is employed in the prophylaxis of gout flares in a human individual, that is, to prevent gout flares. Such treatment can also be referred to as chronic treatment, meaning long-term treatment to reduce the occurrence of gout flares. In one embodiment, the method comprises determining a first colchicine dosage amount adapted for daily oral administration to the gout patient to prevent gout flares in the absence of concomitant administration of clarithromycin or erythromycin, determining a second colchicine dosage amount that is a 50% to 75% reduction of the first colchicine dosage amount, and orally administering the second colchicine dosage amount to the gout patient who is concomitantly receiving administration of clarithromycin or erythromycin. The second colchicine dosage amount is administered to the patient in one or more doses one or more times per day every day, or double the second colchicine dosage amount is administered to the patient in one or more doses per day every other day.

In certain embodiments, in this method, the 50% to 75% reduction comprises one or more of 1) reducing the number of doses of colchicine administered per day, 2) reducing the amount of colchicine administered per dose, and 3) reducing the administration of colchicine from administration every day to administration every other day. For example, in this method, the 50% to 75% reduction may comprise reducing both the number of doses of colchicine administered per day and the amount of colchicine administered per dose.

In other aspects of these embodiments, one or more (where not mutually exclusive) of the following applies: 1) the patient is administered each dose of colchicine as one 0.6 mg colchicine tablet or as one half of a 0.6 mg colchicine tablet, 2) the patient is an adult, 3) the adult patient is less than 70 years old, 4) the patient is receiving concomitant administration of clarithromycin, 6) the second colchicine dosage amount is a one-half reduction of the first colchicine dosage amount, 7) the second colchicine dosage amount is a two-thirds reduction of the first colchicine dosage amount, 8) the second colchicine dosage amount is a three-quarters reduction of the first colchicine dosage amount, 9) the first colchicine dosage amount is about 1.2 mg per day and the second colchicine dosage amount is about 0.3 mg per day, 10) the first colchicine dosage amount is about 0.6 mg per day and the second colchicine dosage amount is about 0.15 mg per day.

In aspects of these embodiments, the second colchicine dosage amount of about 0.3 mg per day is administered as one half of a 0.6 mg colchicine tablet once a day every day, and the second colchicine dosage amount of about 0.15 mg per day is administered as one half of a 0.6 mg colchicine tablet once a day every other day.

In one embodiment, a method of using colchicine for prophylactic treatment of gout flares in a human gout patient so as to reduce the occurrence of colchicine toxicity when said patient is receiving concomitant administration of clarithromycin or erythromycin, comprises: orally administering a second colchicine daily dosage amount for prophylactic treatment of gout flares to the human gout patient who is concomitantly receiving administration of clarithromycin or erythromycin, wherein the second colchicine daily dosage amount is a 50 to 75% reduction of a first colchicine daily dosage amount suitable for daily oral administration for the prophylactic treatment of gout flares in the absence of concomitant administration of clarithromycin or erythromycin, wherein concomitant administration of clarithromycin or erythromycin is administration within 1 to 2 days of orally administering the second colchicine dosage amount, and wherein the first colchicine daily dosage amount is 1.2 mg administered as two 0.6 mg doses per day, or the first colchicine daily dosage amount is 0.6 mg per day.

In another embodiment, a method of using colchicine for prophylactic treatment of gout flares in a human gout patient so as to reduce the occurrence of colchicine toxicity when said patient is receiving concomitant administration of clarithromycin or erythromycin, comprises: orally administering a second colchicine daily dosage amount for prophylactic treatment of gout flares to the human gout patient who is concomitantly receiving administration of clarithromycin or erythromycin, wherein the second colchicine daily dosage amount is a 75% reduction of a first colchicine daily dosage amount suitable for daily oral administration for the prophylactic treatment of gout flares in the absence of concomitant administration of clarithromycin or erythromycin, wherein concomitant administration of clarithromycin or erythromycin is administration within 1 to 2 days of orally administering the second colchicine dosage amount. In certain embodiments, the first colchicine daily dosage amount is 1.2 mg administered as two 0.6 mg doses per day, or the first colchicine daily dosage amount is 0.6 mg per day.

In another embodiment, a method of using colchicine for prophylactic treatment of gout flares in an adult human gout patient so as to reduce the occurrence of colchicine toxicity when said patient is receiving concomitant administration of clarithromycin or erythromycin comprises administering a reduced colchicine daily dosage amount to the patient for prophylactic treatment of gout flares, wherein the reduced colchicine daily dosage amount is 50-75% of a manufacturers' recommended colchicine daily dosage amount for the prophylactic treatment of gout flares in the absence of concomitant clarithromycin or erythromycin administration, wherein concomitant administration of clarithromycin or erythromycin is administration within 1 to 2 days of orally administering the second colchicine dosage amount. In certain embodiments, the manufacturers' recommended colchicine daily dosage amount for the prophylactic treatment of gout flares in the absence of concomitant clarithromycin or erythromycin administration is 1.2 mg/day or 0.6 mg/day.

In another embodiment, a method of using colchicine for prophylactic treatment of gout flares in an adult human gout patient so as to reduce the occurrence of colchicine toxicity when said patient is receiving concomitant administration of clarithromycin or erythromycin comprises administering a reduced colchicine daily dosage amount to the patient for prophylactic treatment of gout flares, wherein the reduced colchicine daily dosage amount is 75% of a manufacturers' recommended colchicine daily dosage amount for the prophylactic treatment of gout flares in the absence of concomitant clarithromycin or erythromycin administration, wherein concomitant administration of clarithromycin or erythromycin is administration within 1 to 2 days of orally administering the second colchicine dosage amount.

In one embodiment, the daily colchicine is coadministered with a urate-lowering drug such as febuxostat or allopurinol. Daily dosage amounts of febuxostat are typically 40 mg or 80 mg once daily. Daily dosage amounts of allopurinol are 200 to 300 mg per day for patients with mild gout and 400 to 600 mg per day for those with moderately severe tophaceous gout. The appropriate dosage amount may be administered in divided doses or as a single equivalent dose with the 300 mg tablet. Dosage requirements in excess of 300 mg should be administered in divided doses. The minimal effective dosage amount is 100 to 200 mg daily and the maximal recommended dosage amount is 800 mg daily. To reduce the possibility of flare-up of acute gouty attacks, it is recommended that the patient start with a low dosage amount of allopurinol (100 mg daily) and increase at weekly intervals by 100 mg until a serum uric acid level of 6 mg/dL or less is attained but without exceeding the maximal recommended dosage amount.

In yet another embodiment, a method of using colchicine for prophylactic treatment of gout flares in a human gout patient that is also receiving treatment with urate-lowering therapy so as to reduce the occurrence of colchicine toxicity when said patient is receiving concomitant administration of clarithromycin or erythromycin, comprises: orally administering a second colchicine daily dosage amount for prophylactic treatment of gout flares to the human gout patient who is concomitantly receiving administration of clarithromycin or erythromycin, wherein the second colchicine daily dosage amount is a 75% reduction of a first colchicine daily dosage amount suitable for daily oral administration for the prophylactic treatment of gout flares in the absence of concomitant administration of clarithromycin or erythromycin, wherein concomitant administration of clarithromycin or erythromycin is administration within 1 to 2 days of orally administering the second colchicine dosage amount. In certain embodiments, the first colchicine daily dosage amount is 1.2 mg administered as two 0.6 mg doses per day, or the first colchicine daily dosage amount is 0.6 mg per day. In certain embodiments, the urate lowering therapy is allopurinol or febuxostat.

In another embodiment, colchicine is used for the treatment of acute gout, that is, treatment of gout flares. In one embodiment, the method comprises determining a first colchicine dosage amount adapted for oral administration to the gout patient to treat gout flares in the absence of concomitant administration of clarithromycin or erythromycin, determining a second colchicine dosage amount that is a 50% to 75% reduction, preferably a two-thirds or three quarters reduction, of the first colchicine dosage amount, and orally administering the second colchicine dosage amount to the gout patient who is concomitantly receiving administration of clarithromycin or erythromycin. In one embodiment, the colchicine administration is not repeated for at least three days.

In certain embodiments, the 50% to 75% reduction comprises one or more of 1) reducing the number of doses of colchicine administered (e.g., per day), 2) reducing the amount of colchicine administered per dose (i.e., reducing the size of at least one colchicine dose), and 3) reducing the administration of colchicine from administration every day to administration every other day. For example, in this method, the 50% to 75% reduction may comprise reducing both the number of doses of colchicine administered per day and the amount of colchicine administered per dose. In one embodiment, the colchicine administration is not repeated for at least three days.

In other aspects of these embodiments, one or more (where not mutually exclusive) of the following apply: 1) the patient is administered each dose of colchicine as one 0.6 mg colchicine tablet or as one half of a 0.6 mg colchicine tablet (e.g. one half a scored 0.6 mg colchicine tablet), 2) the patient is an adult, 3) the adult patient is less than 70 years old, 4) the patient is receiving concomitant administration of clarithromycin, 5) the second colchicine dosage amount is about a one-half reduction of the first colchicine dosage amount, 6) the second colchicine dosage amount is about a two-thirds reduction of the first colchicine dosage amount, 7) the second colchicine dosage amount is about a three-quarters reduction of the first colchicine dosage amount, 8) the first colchicine dosage amount is about 1.8 mg per day and the second colchicine dosage amount is about 0.6 mg per day, 9) the second colchicine dosage amount is a single dose of about 0.6 mg, and after administration of the single dose ingestion of colchicine is stopped until a subsequent gout flare occurs, 10) the second colchicine dosage amount is a single dose of about 0.6 mg of colchicine, and after administration of the single dose ingestion of colchicine is not repeated within a 3-day period.

In an additional embodiment, the first colchicine dosage amount is about 1.8 mg per day and the second colchicine dosage amount is a single 0.6 mg dose, and preferably ingestion of colchicine is not repeated for at least three days after the single dose is administered.

In another embodiment, a method of using colchicine to treat a gout flare in a human patient who is receiving concomitant administration of clarithromycin or erythromycin comprises determining a first colchicine dosage amount adapted for oral administration to the patient to treat a gout flare in the absence of concomitant administration of clarithromycin or erythromycin, determining a second colchicine dosage amount that is a 50-75% reduction of the first colchicine dosage amount, and orally administering the second colchicine dosage amount to the patient who is experiencing a gout flare and is concomitantly receiving administration of clarithromycin or erythromycin, wherein concomitant administration of clarithromycin or erythromycin is administration within 1 to 2 days of orally administering the second colchicine dosage amount, and not repeating colchicine administration for at least three days.

In another embodiment, a method of using colchicine to treat a gout flare in a human patient who is receiving concomitant administration of clarithromycin or erythromycin comprises determining a first colchicine dosage amount adapted for oral administration to the patient to treat a gout flare in the absence of concomitant administration of clarithromycin or erythromycin, determining a second colchicine dosage amount that is about a two thirds reduction of the first colchicine dosage amount, and orally administering the second colchicine dosage amount to the patient who is experiencing a gout flare and is concomitantly receiving administration of clarithromycin or erythromycin, wherein concomitant administration of clarithromycin or erythromycin is administration within 1 to 2 days of orally administering the second colchicine dosage amount, and not repeating colchicine administration for at least three days.

In another embodiment, a method of using colchicine to treat a gout flare in an adult human gout patient so as to reduce the occurrence of colchicine toxicity when said patient is receiving concomitant administration of clarithromycin or erythromycin comprises administering a reduced colchicine dosage amount to the patient to treat gout flares, wherein the reduced colchicine dosage amount is about 50% to about 75% of a manufacturer's recommended colchicine dosage amount in the absence of concomitant clarithromycin or erythromycin administration, and not repeating colchicine administration for at least three days, wherein concomitant administration of clarithromycin or erythromycin is administration within 1 to 2 days of orally administering the second colchicine dosage amount.

In a one embodiment, the patient is administered the colchicine according to a colchicine dosing regimen of a single starting colchicine dose of no more than about 0.6 mg colchicine, followed by either no additional colchicine doses within about 12, 24, 48, or 72 hours, or followed by at least one additional colchicine dose within 12 hours and no more frequently than once every hour (e.g., every 3, 4, 6, 8, or 12 hours). In this embodiment, each additional colchicine dose is no greater than about 0.3 mg and the patient may be an adult patient or a pediatric patient. In one embodiment, the starting colchicine dose is about 0.6 mg or about 0.3 mg, and each additional colchicine dose is about 0.3 mg. When additional doses are administered, it is preferred that only two, three, or four additional colchicine doses are administered within about 24 hours. In another embodiment, the patient is an adult patient and the starting colchicine dose is about 0.6 mg and each additional colchicine dose, if any, is about 0.3 mg. In one embodiment only three additional colchicine doses are administered within about 24 hours.

In another embodiment, colchicine is administered to a patient suffering from a condition treatable with colchicine, and the concomitant macrolide antibiotic is administered concurrently, or the patient has recently completed a dosing regimen of a macrolide antibiotic to treat an infection, and the patient is (immediately or within a period of two weeks, preferably three days, more preferably within 48 hours or 24 hours after completion of the macrolide antibiotic dosing regimen) administered a single dose of no more than about 0.6 mg of colchicine, preferably 0.3 mg or 0.6 mg of colchicine. For example, the starting colchicine dose is about 0.6 mg and only one additional colchicine dose is administered within about 24 hours and the additional colchicine dose is about 0.6 mg.

A preferred antibiotic for use in the disclosed methods is one that is an inhibitor of either or both of CYP3A and P-glycoprotein, preferably both. In certain embodiments, the antibiotic is dirithromycin, erythromycin, roxithromycin, or more preferably, clarithromycin or erythromycin. The clarithromycin may be administered to the patient at a dosage amount of about 500 mg daily and the colchicine dosing regimen is one about 0.6 mg colchicine dose to start, followed by 0, 1, 2, 3, or 4 additional colchicine doses of about 0.6 mg every 1, 2, 3, 4, 5, 6, 7, 8, 9, 10, 11, or 12 hours (e.g., every 2, 3, 4, 5, or 6 hours) after the preceding colchicine dose. Alternately, the clarithromycin may be administered to the patient at a dosage amount of about 1000 mg daily and the colchicine dosing regimen is one about 0.3 mg colchicine dose to start, followed by 0, 1, 2, 3, or 4 additional colchicine doses of about 0.3 mg each every 2, 3, 4, 5, 6, 7, 8, 9, 10, 11, or 12 hours (e.g., every 3, 4, 5, or 6 hours) after the preceding colchicine dose. In a preferred regimen for treatment of acute gout flares, ingestion of colchicine is continued until a total of no more than about 1.2, 1.4, 1.6, 1.8, 2, or 2.4 mg of colchicine has been ingested, after which ingestion of colchicine is stopped until a subsequent acute gout flare occurs. In still another preferred regimen, clarithromycin may be administered to a patient, e.g., at a dosage amount of about 250 mg B.I.D. for a period of about 7 to 10 days, and the colchicine dosing regimen is administered to the patient upon completion of the clarithromycin dosing regimen, wherein the colchicine dosing regimen consists of the administration of no more than one dose of no more than 0.6 mg of colchicine. In one embodiment, the colchicine is administered as a dosage form of 0.6 mg (e.g., one 0.6 mg colchicine tablet), or 0.3 mg (e.g., one half of a 0.6 mg tablet) of colchicine and administration of the dosage form is not repeated within a period of at least about two days, preferably at least about three days.

In these and other embodiments, the colchicine-responsive condition is gout (e.g. a gout flare in a chronic gout sufferer), familial Mediterranean fever (FMF), thrombocytopenic purpura, pericarditis, scleroderma, or Behcet's disease. The gout may be an acute gout flare or chronic gout. For gout, the dosing regimen is generally continued until a total of no more than 2.4 mg of colchicine has been ingested, after which ingestion of colchicine is stopped until a subsequent gout flare occurs.

Another embodiment comprises administering colchicine to a patient also taking clarithromycin, or having completed treatment with clarithromycin within the prior 14 days, the patient being administered a single dosage amount of about 0.6 mg or about 0.3 mg of colchicine to treat a gout flare, which administration is not repeated within any 3-day period.

In another aspect, herein disclosed is a method for increasing the blood plasma levels of colchicine in a patient to whom colchicine is being administered to treat or prevent a colchicine-responsive condition. This method comprises the concomitant dosing of the patient with a sufficient amount of a macrolide antibiotic to increase the $C_{max}$ of colchicine by about 167% to 200%, or to increase the AUC of colchicine in the patient by about 240% to 250%, or to increase the plasma half-life of colchicine by about 233%, or to decrease the clearance of colchicine by about 75%, compared to the $C_{max}$, AUC, plasma half-life, or clearance in the same or a matched patient when not being administered a concomitant macrolide antibiotic. In a one embodiment, the patient is being administered no more than three hourly doses of about 0.6 mg of colchicine or less, the macrolide antibiotic is clarithromycin, and the amount of macrolide antibiotic is from about 500 mg to about 1000 mg, with about 500 mg being preferred.

In another aspect, herein disclosed are methods for using colchicine which methods involve the use of pharmacy management systems.

In one aspect one such method comprises a pharmacy receiving a prescription for colchicine for a patient who is suffering from gout (e.g., acute gout flares or chronic gout) and who is concomitantly being treated with a macrolide antibiotic that is an inhibitor of CYP3A and P-glycoprotein, followed by the pharmacy dispensing colchicine in response to receipt of the prescription, wherein the dispensing is preceded by entry into a first computer readable storage medium, in functional communication with a computer, of a unique patient identifier for said patient and at least one drug identifier for colchicine linked to the patient identifier so as to indicate that colchicine is to be administered to the patient. The computer is programmed to issue a drug-drug interaction alert when the at least one drug identifier for colchicine is entered linked to the patient identifier so as to indicate that colchicine is to be administered to the patient and when the patient identifier is also linked to an identifier indicating that a macrolide antibiotic that is an inhibitor of CYP3A or P-glycoprotein is being concomitantly administered to the patient. Upon entry of the at least one drug identifier for colchicine linked to the patient identifier, a drug-drug interaction alert is issued to one or more of a pharmacy technician, a pharmacist, or a pharmacy customer obtaining the colchicine, said alert indicating that a macrolide antibiotic is being concomitantly administered to the patient and that prior to the colchicine being dispensed, the colchicine dosing regimen must be reviewed and, if necessary adjusted, so that when the colchicine is delivered to the pharmacy customer obtaining the colchicine it is delivered along with instructions for the colchicine to be taken in accordance with a dosing regimen of no more than one about 0.6 mg colchicine dose to start (e.g., following the onset of the acute gout attack or the first sign of a gout flare) followed by either: no additional colchicine doses within about 12, 24, 48, or 72 hours, or at least one additional colchicine dose within about 12 hours and no more frequently than once every hour and wherein each additional colchicine dose is no greater than about 0.6 mg, and wherein the patient ingests the colchicine as instructed.

The drug-drug interaction alert may be issued as one or both of a written warning on a display screen of the pharmacy management computer system, and a printed warning. The printed warning may be attached to or packaged with the dispensed prescription.

In one aspect, the identifier indicating that a macrolide antibiotic is being concomitantly administered to the patient is an identifier indicating that the macrolide antibiotic is clarithromycin and is linked to at least one further identifier indicating that the clarithromycin is prescribed so that 500 mg of clarithromycin is to be ingested by the patient daily, in which case the dosing regimen for colchicine is preferably one about 0.6 mg colchicine dose to start, optionally followed by additional colchicine doses, e.g., 0, 1, 2, 3, or 4 additional colchicine doses within 24 hours of about 0.3 mg ingested every 1, 2, 3, 4, 5, 6, 7, 8, 9 10, 11, or 12 hours (e.g., every 2, 3, 4, 5, or 6 hours) after the preceding colchicine dose. In another embodiment, the identifier indicating that a macrolide antibiotic is being concomitantly administered to the patient is an identifier indicating that the macrolide antibiotic is clarithromycin is linked to at least one further identifier, entered into a second computer readable storage medium in functional communication with a computer, the second storage medium being the same as or different from the first storage medium, and the further identifier indicating that the clarithromycin is prescribed so that about 500 mg of clarithromycin is to be ingested by the patient daily, in which case the colchicine dosing regimen is (preferably) one about 0.6 mg colchicine dose to start, followed by an about 0.3 mg colchicine dose ingested every 1, 2, 3, 4, 5, 6, 7, 8, 9, 10, 11, or 12 hours (e.g., every six to eight hours) after the preceding colchicine dose.

In yet another aspect, the identifier indicating that a macrolide antibiotic is being concomitantly administered to the patient is an identifier indicating that the macrolide antibiotic is clarithromycin and is linked to at least one further identifier, entered into a second computer readable storage medium in functional communication with a computer, the second storage medium being the same as or different from the first storage medium, and the further identifier indicating that the clarithromycin is prescribed so that about 1000 mg of clarithromycin is to be ingested by the patient daily and the dosing regimen is one about 0.3 mg colchicine dose to start, followed by an about 0.3 mg colchicine dose ingested every 2, 3, 4, 5, 6, 7, or 8 hours (e.g., every eight to twelve hours) after the preceding colchicine dose.

One dosing regimen calls for ingestion of colchicine to be continued until a total of no more than 1.2 mg or 2.4 mg of colchicine has been ingested, after which ingestion of colchicine is to be stopped, e.g., for at least 2, 3, 4, 5, 6, or 7 days, or until a subsequent acute gout flare, or the first sign of a subsequent gout flare, occurs.

Also disclosed herein is a dosage amount adjustment method for administering colchicine to a patient to treat a medical condition, the patient concomitantly suffering from an infection amenable to treatment with a macrolide antibiotic. The method comprises determining a first, a second, and a subsequent monotherapy colchicine dosage amount and a colchicine treatment schedule; and determining an antibiotic dosage amount and an antibiotic treatment schedule; and administering the macrolide antibiotic to the patient at the antibiotic dosage amount according to the antibiotic treatment schedule while concomitantly administering colchicine to the patient according to the colchicine treatment schedule at a first, a second, and a subsequent polytherapy colchicine dosage amount, each of which is a fraction of each of the corresponding first, second, and subsequent monotherapy colchicine dosage amounts, the fraction being less than or equal to about $2/3$.

An alternate embodiment of this method comprises determining a monotherapy colchicine dosage amount and a colchicine treatment schedule, each adapted so that, when colchicine is administered to the patient in the absence of concomitant administration of the antibiotic at the monotherapy colchicine dosage amount according to the colchicine treatment schedule, a therapeutic circulating plasma level of colchicine is predicted to be achieved in the patient that is safe and effective to treat the condition in the patient while posing an acceptable adverse effect risk; and determining an antibiotic dose and an antibiotic treatment schedule, each adapted so that, when the antibiotic is administered to the patient at the antibiotic dosage amount according to the antibiotic treatment schedule, a circulating level of the antibiotic is predicted to be achieved in the patient that is safe and therapeutically effective to treat the infection in the patient and administering the antibiotic to the patient at the antibiotic dosage amount according to the antibiotic treatment schedule while concomitantly administering colchicine to the patient at a polytherapy colchicine dosage amount that is a fraction less than or equal to $1/2$ of the monotherapy colchicine dosage amount to the patient according to the colchicine treatment schedule.

According to this embodiment, upon the administering of the antibiotic to the patient at the antibiotic dosage amount according to the antibiotic treatment schedule while concomitantly administering colchicine to the patient at the polytherapy colchicine dose according to the colchicine treatment schedule, the therapeutic circulating level of colchicine is achieved in the patient. Preferably, the fraction is selected from $1/12$, $1/6$, $1/4$, $1/3$, $5/12$, and $1/2$, more preferably, the fraction is $1/3$ or $1/2$. Preferably the antibiotic is selected from clarithromycin, dirithromycin, erythromycin and roxithromycin. Exemplary conditions are selected from gout, FMF, thrombocytopenic purpura, and Behçet's disease. In a preferred embodiment, the gout is an acute gout flare and the colchicine treatment schedule is an acute treatment schedule adapted for treatment of acute gout flares, or the gout is chronic gout, and the colchicine treatment schedule is a chronic treatment schedule adapted for prophylaxis of flares. In another embodiment, the fraction is $1/3$ or $1/2$ and treatment with colchicine is initiated subsequent to initiation of treatment with clarithromycin.

In one embodiment, each of the monotherapy colchicine doses and the colchicine treatment schedule are each adapted so that, when colchicine is administered to the patient at the monotherapy colchicine dose according to the colchicine treatment schedule in the absence of concomitant administration of the antibiotic, a therapeutic circulating level of colchicine is predicted to be achieved in the patient that is predicted to be safe and effective to treat the condition in the patient while posing an acceptable adverse effect risk.

Alternately, the antibiotic dose and the antibiotic treatment schedule are each adapted so that, when the antibiotic is administered to the patient at the antibiotic dose according to the antibiotic treatment schedule a circulating level of the antibiotic is predicted to be achieved in the patient that is therapeutically effective to treat the infection in the patient.

In one embodiment, upon the administration of the antibiotic to the patient at the antibiotic dose according to the antibiotic treatment schedule while concomitantly administering colchicine to the patient according to the colchicine treatment schedule at the polytherapy colchicine dose, a therapeutic circulating level of colchicine is predicted to be achieved in the patient that is predicted to be safe and effective to treat the condition in the patient while posing an acceptable adverse effect risk. In one embodiment, each subsequent colchicine dose is the same as the second colchicine dose. In another embodiment, each of the second and subsequent colchicine doses are the same as the first colchicine dosage amounts. In another, the fraction is selected from about $1/12$, about $1/6$, about $1/4$, about $1/3$, about $5/12$, about $1/2$, and about $7/12$, e.g., about $1/2$ or about $2/3$. In certain embodiments, the colchicine treatment schedule is once-a-day, twice-a-day, three-times-a-day or four-times-a-day.

Acute Gout

Acute gout, or gout flares, can be treated according to the following treatment schedule. This table indicates the original, or intended, dosage amount, i.e., the dosage amount of colchicine recommended absent concomitant administration of the drugs listed below. This table also presents the dosage amount adjustment, or the recommended colchicine dosage amount to be administered when strong and moderate CYP3A4 and P-gp inhibitors are administered concomitantly with colchicine when the patient is being treated for a gout flare.

| | Colchicine Dose Recommendation | |
|---|---|---|
| Drug | Original Intended Dose (Total Dose) | Dose Adjustment |
| Strong CYP3A4 Inhibitors | Regimen Reduced by Two Thirds | |
| Clarithromycin | 1.2 mg (2 tablets) at the first sign of the flare followed by 0.6 mg (1 tablet) one hour later. | 0.6 mg (1 tablet) × 1 dose. Dose to be repeated no earlier than 3 days. |
| Erythromycin | Dose to be repeated no earlier than 3 days. | |

Chronic Gout

For chronic gout (prophylaxis of gout flares), an original intended daily dosage amount is 1.2 mg or 6 mg. Alternatively, an intended daily dosage amount of chronic gout can be as much as 2.4 mg per day. The daily dosage amount for chronic gout can be administered at one time or dosed at intervals throughout the day, e.g. twice daily, three times daily, or four times daily.

Chronic gout, with and without a concomitant dose of another drug, can be treated according to the following treatment schedule:

| Colchicine Dose Adjustment for Co-administration with Interacting Drugs If No Alternative Available | | |
|---|---|---|
| | Colchicine Dose Recommendation | |
| Drug | Original Intended Dose | Dose Adjustment |
| Clarithromycin | 0.6 mg twice daily | 0.3 mg once daily |
| | 0.6 mg once daily | 0.3 mg once every other day |
| Erythromycin | 0.6 mg twice daily | 0.3 mg once daily |
| | 0.6 mg once daily | 0.3 mg once every other day |

The dosage amount of 0.3 mg once every other day is administered either as 0.3 mg once every other day or 0.15 mg once a day.

Familial Mediterranean Fever

Familial Mediterranean Fever (FMF) can be treated according to the following intended daily dosing schedule:

| | Daily dosage amount | |
|---|---|---|
| Age | Usual | Maximum |
| Adults and children >12 years | 1.2 mg | 2.4 mg |
| Children >6 to 12 years | 0.9 mg | 1.8 mg |
| Children 4 to 6 years | 0.3 mg | 1.8 mg |

When colchicine is given to patients with FMF concomitantly with other drugs, the adjusted (reduced) dosage amount of colchicine, according to this embodiment, is provided in the table below:

| Concomitant Drug Class or Food | Noted or Anticipated Outcome | Clinical Comment |
|---|---|---|
| Strong CYP3A4 Inhibitors: clarithromycin | Significant increase in colchicine plasma levels[1]; fatal colchicine toxicity has been reported with clarithromycin, a strong CYP3A4 inhibitor. Similarly, significant increase in colchicine plasma levels is anticipated with other strong CYP3A4 inhibitors. | Use colchicine with caution at reduced maximum dose of 0.3 mg twice daily with increased monitoring for adverse effects. In patients with renal or hepatic impairment, use of colchicine in conjunction with these drugs is contraindicated. |
| Moderate CYP3A4 inhibitors: erythromycin | Significant increase in colchicine plasma concentration is anticipated. Neuromuscular toxicity has been reported with diltiazem and verapamil interactions. | Use colchicine with caution at reduced maximum dose of 0.6 mg twice daily with increased monitoring for adverse effects. In patients with renal or hepatic impairment, use a maximum dose of 0.3 mg twice daily. |

Colchicine is one of the most widely used drugs for treating familial Mediterranean fever (FMF). It has been reported that 5-10% of FMF patients do not show a beneficial response to colchicine administration. A polymorphism in the ABCB1 gene, the "ABCB1 3435 C to T polymorphism" has been reported to correlate with this lack of response to colchicine treatment, with patients with the homozygous TT genotype exhibiting the most pronounced "non-responder" phenotypes.

Accordingly, in another aspect, provided herein is a method for treating a patient suffering from FMF, which patient is a colchicine non-responder. In one embodiment, the patient is homozygous for the TT genotype of the ABCB1 3435 C to T polymorphism. The method entails the concomitant administration of a Pgp inhibitor and colchicine to the patient. A preferred Pgp inhibitor for use in this method is verapamil or cyclosporine-A, more preferably a macrolide antibiotic, preferably dirithromycin, erythromycin or roxithromycin, or, more preferably clarithromycin. Dosage amounts of the Pgp inhibitor for this purpose correspond to those called for in the prescribing information for the drug in question. For clarithromycin, the dosage amounts are 500 to 1000 mg per day and duration of clarithromycin dosing is preferably one, two, or three days, repeated weekly or bi-weekly. Preferred colchicine dosing regimens for this purpose are the same as used for treatment of FMF in responders, though the doses of colchicine administered may be increased as tolerated, e.g., up to two to three times the typical doses.

These and other embodiments, advantages and features of the present invention are further elaborated herein below.

DETAILED DESCRIPTION

Following multiple oral doses (0.6 mg twice daily), the mean elimination half-life of colchicine in young healthy volunteers (mean age 25 to 28 years of age) is 26.6 to 31.2 hours.

Pharmacy management systems are computer-based systems that are widely used by commercial pharmacies to manage prescriptions and to provide pharmacy and medical personnel with warnings and guidance regarding drugs being administered to patients. Such systems typically provide alerts warning either or both of health care providers and patients when a drug that may be harmful to the particular patient is prescribed. For example, such systems can provide alerts warning that a patient has an allergy to a prescribed drug, or is receiving concomitant administration of a drug that can have a dangerous interaction with a prescribed drug. U.S. Pat. Nos. 5,758,095, 5,833,599, 5,845,255, 6,014,631, 6,067,524, 6,112,182, 6,317,719, 6,356,873, and 7,072,840, each of which is incorporated herein by reference, disclose various pharmacy management systems and aspects thereof. Many pharmacy management systems are now commercially available, e.g., CENTRICITY Pharmacy from BDM Information Systems Ltd., General Electric Healthcare, Waukesha, Wis., Rx30 Pharmacy Systems from Transaction Data Systems, Inc., Ocoee, Fla., SPEED SCRIPT from Digital Simplistics, Inc., Lenexa, Kans., and various pharmacy management systems from OPUS-ISM, Hauppauge, N.Y.

In the specification and claims that follow, references will be made to a number of terms which shall be defined to have the following meaning.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

"Concomitant" and "concomitantly" as used herein refer to the administration of at least two drugs to a patient either simultaneously or within a time period during which the effects of the first administered drug are still operative in the patient. Thus, if the first drug is, e.g., clarithromycin and the second drug is colchicine, the concomitant administration of the second drug can occur as much as one to two weeks, preferably within one to seven days, after the administration of the first drug. This is because clarithromycin can exert a long-lasting inhibition of CYP3A isozymes so that CYP3A activity in the patient may not return to pre-clarithromycin-administration levels for as much as two weeks after the cessation of clarithromycin administration. If colchicine is the first drug, administration of a second drug would be concomitant if done within 1 to 2 days, preferably 12 to 24 hours.

"Dosage amount" means an amount of a drug suitable to be taken during a fixed period, usually during one day (i.e., daily).

"Dosage amount adapted for oral administration" means a dosage amount that is of an amount deemed safe and effective for the particular patient under the conditions specified. As used herein and in the claims, this dosage amount is determined by following the recommendations of the drug manufacturer's Prescribing Information as approved by the US Food and Drug Administration.

"Dosing regimen" means the dose of a drug taken at a first time by a patient and the interval (time or symptomatic) and dosage amounts at which any subsequent doses of the drug are taken by the patient. Each dose may be of the same or a different dosage amount.

A "dose" means the measured quantity of a drug to be taken at one time by a patient.

A "patient" means a human or non-human animal in need of medical treatment. Medical treatment can include treatment of an existing condition, such as a disease or disorder, prophylactic or preventative treatment, or diagnostic treatment. In preferred embodiments the patient is human.

"Providing" means giving, administering, selling, distributing, transferring (for profit or not), manufacturing, compounding, or dispensing.

"Risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility.

Pharmacokinetic parameters referred to herein describe the in vivo characteristics of drug (or a metabolite or a surrogate marker for the drug) over time. These include plasma concentration (C), as well as $C_{max}$, $C_n$, $C_{24}$, $T_{max}$, and AUC. "$C_{max}$" is the measured plasma concentration of the active agent at the point of maximum, or peak, concentration. "$C_{min}$" is the measured plasma concentration of the active agent at the point of minimum concentration. "$C_n$" is the measured plasma concentration of the active agent at about n hours after administration. "$C_{24}$" is the measured plasma concentration of the active agent at about 24 hours after administration. The term "$T_{max}$" refers to the time from drug administration until $C_{max}$ is reached. "AUC" is the area under the curve of a graph of the measured plasma concentration of an active agent vs. time, measured from one time point to another time point. For example $AUC_{0-t}$ is the area under the curve of plasma concentration versus time from time 0 to time t, where time 0 is the time of initial administration of the drug. Time t can be the last time point with measurable plasma concentration for an individual formulation. The $AUC_{0-\infty}$ or $AUC_{0-INF}$ is the calculated area under the curve of plasma concentration versus time from time 0 to time infinity. In steady-state studies, $AUC_{0-\tau}$ is the area under the curve of plasma concentration over the dosing interval (i.e., from time 0 to time $\tau$ (tau), where tau is the length of the dosing interval. Other pharmacokinetic parameters are the parameter $K_e$ or $K_{el}$, the terminal elimination rate constant calculated from a semi-log plot of the plasma concentration versus time curve; $t_{1/2}$ the terminal elimination half-life, calculated as $0.693/K_{el}$. CL/F denotes the apparent total body clearance after administration, calculated as Total Dose/Total $AUC_\infty$; and $V_{area}/F$ denotes the apparent total volume of distribution after administration, calculated as Total Dose/(Total $AUC_\infty \times K_{el}$).

"Side effect" means a secondary effect resulting from taking a drug. The secondary effect can be a negative (unfavorable) effect (i.e., an adverse side effect) or a positive (favorable) effect.

The most frequently reported adverse side effects to colchicine therapy are gastrointestinal, specifically abdominal pain with cramps, diarrhea, nausea, and vomiting. Less frequently or rarely reported adverse side effects associated with colchicine therapy include anorexia, agranulocytosis, allergic dermatitis, allergic reactions, alopecia, angioedema, aplastic anemia, bone marrow depression, myopathy, neuropathy, skin rash, thrombocytopenic disorder, and urticaria.

Whether a patient experiences an adverse side effect can be determined by obtaining information from the patient regarding onset of certain symptoms which may be indicative of the adverse side effect, results of diagnostic tests indicative of the adverse side effect, and the like.

The following examples further illustrate aspects of this disclosure but should not be construed as in any way limiting its scope. In particular, the conditions are merely exemplary and can be readily varied by one of ordinary skill in the art.

EXAMPLES

Example 1

Pharmacokinetic Study in Healthy Adults of Single vs. Multiple Oral Doses of Colchicine Tablets This study was a single-center, open-label, single-sequence, two-period study to evaluate the pharmacokinetic profile of colchicine following single and multiple oral doses of colchicine tablets, 0.6 mg, in healthy volunteers.

In Period 1, study subjects received a 0.6-mg dose of colchicine after an overnight fast of at least 10 hours. In Period 2, subjects received a 0.6-mg dose of colchicine in the morning and the evening (approximately 12 hours later) for 10 days (steady state regimen). Subjects received a light breakfast served 60 minutes following dose administration in the morning and the evening dose was administered 90 minutes after an evening meal on Days 15 through 24 only. On Day 25, the colchicine dose was administered after an overnight fast of at least 10 hours and lunch was served 4 hours post-dose. Study periods were separated by a 14-day washout. Following the single dose and the last dose of the multiple dose regimen (beginning on the mornings of Day 1 and Day 25, respectively), blood samples were collected (6 mL each) from each subject within 1 hour prior to dosing and after dose administration at study hours 0.5, 1, 1.5, 2, 3, 4, 6, 8, 10, 12, and 24 (while confined) and 36, 48, 72, and 96 (on an outpatient basis). Plasma concentrations of colchicine and its metabolites were determined using validated LC/MS-MS methods.

Thirteen healthy, non-smoking subjects with a mean age of 25.5 years (range 19 to 38 years) and within 15% of ideal body weight were enrolled in this study. All subjects completed both dosing periods according to protocol.

After a single dose, plasma concentrations are no longer quantifiable 24 hours post-dose in all but 1 subject. After the last dose of the steady state regimen, concentrations remained quantifiable for 48 to 72 hours. Review of individual subject data shows that no subject experienced a secondary colchicine peak, either following a single dose or upon multiple dosing.

All 2-O-demethylcolchicine (2-DMC) concentrations were below the level of quantitation (LOQ, 0.2 ng/mL) and only one sample from 1 subject (of 13 subjects) had a detectable 3-O-demethylcolchciine (3-DMC) concentration, which was near the level of quantitation. Therefore, metabolites are not discussed further.

In healthy adults, colchicine appears to be readily absorbed when given orally, reaching a mean maximum plasma concentration of 2.5 ng/mL in 1.5 hours after a single dose. The drug is distributed widely, with an apparent volume of distribution of 540 L, greatly exceeding total body water. The elimination half-life as calculated following a single oral dose is approximately 5 hours. Levels were not detectable by 24 hours post-dose and this is therefore not an accurate estimate. Pharmacokinetic parameter values are summarized in the table below.

Review of trough plasma concentrations indicates that steady state was attained by approximately the eighth day of dosing for most subjects. Colchicine may have a diurnal variation reflected in the observed Cmin concentrations at steady state. Cmin concentrations prior to the morning dose are approximately 12% higher than the Cmin concentrations prior to the evening dose (Day 23 and Day 24). The mean Cmin concentration observed on Day 25 was 0.907 ng/mL.

Colchicine accumulated following administration of multiple doses to an extent greater than expected. Exposure was nearly two-fold higher (approximately 1.7 based on AUC [Day 25 $AUC_{0-\tau}$/Day 1 $AUC_{0-\infty}$] and approximately 1.5 based on Cmax [Day 25 $C_{max}$/Day 1 $C_{max}$]). This observation could be attributable to an underestimation of $AUC_\infty$ following a single dose. With the higher plasma levels that occur with repeated dosing, a longer terminal elimination half life is apparent, 26.6 hours. Pharmacokinetic parameter values are summarized in the tables below.

TABLE 1

Colchicine Pharmacokinetic Parameter Values Following Administration of A Single Oral Dose of Colchicine 0.6 mg in Healthy Adults (N = 13)

|  | $AUC_{0-t}$ (pg-hr/mL) | $AUC_{0-inf}$ (pg-hr/mL) | $C_{max}$ (pg/mL) | $T_{max}$ (hr) | $K_{el}$ (1/hr) | $T_{1/2}$ (hr) |
|---|---|---|---|---|---|---|
| MEAN | 10508.54 | 12281.90 | 2470.77 | 1.50 | 0.1829 | 4.95 |
| STDEV | 3544.82 | 4423.34 | 706.98 | 0.54 | 0.0592 | 4.43 |
| % CV | 33.73 | 36.02 | 28.61 | 36.00 | 32.39 | 89.54 |
| MEDIAN | 10560.90 | 11451.45 | 2714.00 | 1.50 | 0.1992 | 3.48 |
| MIN | 4812.88 | 7252.66 | 1584.00 | 1.00 | 0.0359 | 2.84 |
| MAX | 18128.65 | 23838.48 | 3977.00 | 3.00 | 0.2443 | 19.29 |

TABLE 2

Colchicine Pharmacokinetic Parameter Values Following Administration of Multiple (b.i.d.) Oral Doses of Colchicine 0.6 mg in Healthy Adults (N = 13)

|  | $AUC_{0-t}$ (pg-hr/mL) | $AUC_{0-\tau}$ (pg-hr/mL) | $AUC_{0-inf}$ (pg-hr/mL) | $C_{max}$ (pg/mL) | $C_{min}$ (pg/mL) | $C_{ave}$ (pg/mL) | $T_{max}$ (hr) | $K_{el}$ (1/hr) | $T_{1/2}$ (hr) |
|---|---|---|---|---|---|---|---|---|---|
| MEAN | 43576.96 | 29056.23 | 54198.77 | 3553.15 | 906.51 | 1210.68 | 1.31 | 0.03 | 26.60 |
| STDEV | 9333.26 | 4531.30 | 9214.54 | 843.45 | 152.19 | 188.80 | 0.60 | 0.00 | 4.33 |
| % CV | 21.42 | 15.59 | 17.00 | 23.74 | 16.79 | 15.59 | 45.61 | 16.34 | 16.26 |
| MEDIAN | 41925.10 | 28452.15 | 54113.43 | 3734.00 | 903.50 | 1185.51 | 1.00 | 0.03 | 26.51 |
| MIN | 29328.78 | 20791.98 | 37599.76 | 1977.00 | 636.23 | 866.33 | 0.50 | 0.02 | 20.82 |
| MAX | 58265.35 | 36083.95 | 67944.65 | 4957.00 | 1149.67 | 1503.50 | 3.00 | 0.03 | 33.65 |

TABLE 3

Mean (% CV) Colchicine Pharmacokinetic Parameter Values Following Administration of Single and Multiple (b.i.d.) Oral Doses of Colchicine 0.6 mg in Healthy Adults

|  | Vd/F (L) | CL/F (L/hr) |
|---|---|---|
| Colchicine 0.6-mg Single Dose (N = 13) | | |
| Day 1 | 540.5 (31.0) | 341.5 (54.4) |
| Colchicine 0.6 mg b.i.d. × 10 days | | |
| Day 25 | 1150 (18.73) | 30.3 (19.0) |

CL = Dose/$AUC_{0-t}$ (Calculated from mean values)
Vd = CL/Ke (Calculated from mean values)

In the above table, the parameter CL/F denotes the apparent total body clearance after administration, calculated as Total Dose/Total $AUC0$-$_{tau}$; and $V_d$/F denotes the apparent total volume of distribution after administration, calculated as Total Dose/(Total $AUC_\infty \times K_{el}$).

Example 2

Clinical Drug-Drug Interaction Study of Colchicine and Clarithromycin

A single-center, open-label, one sequence, two-period study was carried out in 23 healthy subjects. On Day 1, a single 0.6-mg dose of colchicine was administered. After completing a 21-day washout period, all subjects received 250 mg of clarithromycin administered twice daily for 7 days (Days 22 through 29), a sufficient dose and duration to inhibit CYP3A4 and Pgp. On the final day (Day 29), a single dose of colchicine was co-administered with the clarithromycin dose.

When combined with steady-state clarithromycin, there is a significant increase in exposure to colchicine as compared to when colchicine is given alone: the mean $C_{max}$ and $AUC_{0-t}$ concentrations increased 167% and 250%, respectively. In addition, co-administration of clarithromycin and colchicine resulted in an increase of 233% in the plasma elimination half-life (t1/2) of colchicine and a 75% decrease in apparent clearance (CL/F). A summary of the mean (% CV) colchicine pharmacokinetic parameters for Day 1 (colchicine administered alone) and Day 29 (colchicine co-administered with steady-state clarithromycin) are given in the table below and illustrated in the table that follows.

TABLE 4

Comparison of Single-Dose Colchicine (0.6 mg, Alone) and Single-Dose Colchicine (0.6 mg) Co-Administered with Steady-State Clarithromycin in Healthy Adults

| DAY | $C_{max}$ (ng/mL) | $T_{max}$[1] (h) | $AUC_{0-t}$ (ng·h/mL) | $AUC_\infty$ (ng·h/mL) | Ke (h$^{-1}$) | Vd/F (L) | CL/F (L/hr) | $t_{1/2}$ (h) |
|---|---|---|---|---|---|---|---|---|
| Colchicine Alone (n = 23) | | | | | | | | |
| 1 | 3 (30.97) | 1.00 (0.5-2.0) | 12 (37.6) | 16 (49.6) | 0.132 (46.87) | 432 (56.1) | 46.8 (43.7) | 9 (126.4) |
| Colchicine + Clarithromycin (n = 23) | | | | | | | | |
| 29 | 8 (23.74) | 1.0 (1.0-5.0) | 42 (23.3) | 53 (22.8) | 0.0298 (90.82) | 493 (33.69) | 12 (23.8) | 30 (41.37) |
| p value | <0.0001 | 0.05061 | <0.0001 | <0.0001 | <0.0001 | <0.0001 | <0.0001 | 0.0001 |

[1] $T_{max}$ mean (range)

Recitation of ranges of values herein are merely intended to serve as a shorthand method of referring individually to each separate value falling within the range, unless otherwise indicated herein, and each separate value is incorporated into the specification as if it were individually recited herein. The endpoints of all ranges directed to the same component or property are inclusive and independently combinable.

All methods described herein can be performed in a suitable order unless otherwise indicated or clearly contradicted by context. The use of any and all examples, or exemplary language (e.g., "such as") herein is intended to better illuminate the disclosure and is non-limiting unless otherwise specified. No language in the specification should be construed as indicating that any non-claimed element as essential to the practice of the claimed embodiments. Unless defined otherwise, technical and scientific terms used herein have the same meaning as is commonly understood by one of skill in the art to which this disclosure belongs. The terms wt %, weight percent, percent by weight, etc. are equivalent and interchangeable Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

What is claimed is:

1. A method of using colchicine to treat a gout flare in an adult human gout patient so as to reduce the occurrence of colchicine toxicity when said patient is receiving concomitant administration of clarithromycin, said method comprising:

orally administering a reduced colchicine dosage amount to the patient to treat gout flares, wherein the reduced colchicine dosage amount is about a 50% to about a 75% reduction of a colchicine dosage amount adapted for oral administration to the gout patient to treat gout flares in the absence of concomitant administration of clarithromycin, and not repeating colchicine administration for at least three days, wherein concomitant administration of clarithromycin is administration within 1 to 2 days of orally administering the reduced colchicine dosage amount.

2. The method of claim 1, wherein the colchicine dosage amount adapted for oral administration to the gout patient to treat gout flares in the absence of concomitant administration of clarithromycin is 1.2 mg at the first sign of a flare, followed by 0.6 mg one hour later.

3. The method of claim 2, wherein the reduced colchicine dosage amount is 0.6 mg at the first sign of a flare, followed by 0.3 mg one hour later.

* * * * *

UNITED STATES PATENT AND TRADEMARK OFFICE
CERTIFICATE OF CORRECTION

| | | |
|---|---|---|
| PATENT NO. | : 8,093,296 B2 | |
| APPLICATION NO. | : 13/090697 | |
| DATED | : January 10, 2012 | |
| INVENTOR(S) | : Matthew W. Davis | |

It is certified that error appears in the above-identified patent and that said Letters Patent is hereby corrected as shown below:

On the Title Page, Item (56), under "OTHER PUBLICATIONS", line 21, delete "Leikin ete;" and insert -- Leikin et --, therefor.

On the Title Page, Item (56), under "OTHER PUBLICATIONS", line 47, delete "Wikidpedia" and insert -- Wikipedia --, therefor.

In column 1, line 12, delete "continuation of part" and insert -- continuation-in-part --, therefor.

In column 3, line 27, delete "*phila.*" and insert -- *phila,* --, therefor.

In column 3, line 32, delete "100" and insert -- 1000 --, therefor.

In column 4, line 14, delete "3-demethylchochicine" and insert -- 3-demethylcolchicine --, therefor.

In column 4, lines 31-32, delete "3-demethylchochicine" and insert -- 3-demethylcolchicine --, therefor.

In column 6, line 22, delete "□" and insert -- ■ --, therefor.

In column 6, line 50, delete "in suffering" and insert -- suffering --, therefor.

In column 7, line 21, delete "6" and insert -- 5 --, therefor.

In column 7, line 23, delete "7" and insert -- 6 --, therefor.

In column 7, line 24, delete "8" and insert -- 7 --, therefor.

In column 7, line 26, delete "9" and insert -- 8 --, therefor.

Signed and Sealed this
Sixteenth Day of October, 2012

David J. Kappos
*Director of the United States Patent and Trademark Office*

CERTIFICATE OF CORRECTION (continued)
U.S. Pat. No. 8,093,296 B2

In column 7, line 28, delete "10" and insert -- 9 --, therefor.

In column 10, line 44, delete "a one" and insert -- one --, therefor.

In column 12, line 4, delete "a one" and insert -- one --, therefor.

In column 13, line 3, after "clarithromycin" insert -- and --.

In column 15, line 36, delete "6" and insert -- 0.6 --, therefor.

In column 15, line 37, delete "of" and insert -- for --, therefor.

In column 16, line 48, delete "levels[1]" and insert -- levels --, therefor.

In column 20, line 37, delete "3-O-demethylcolchciine" and insert -- 3-O-demethylcolchicine --, therefor.

In column 21, line 37, delete "Vd/F" and insert -- $V_d/F$ --, therefor.

In column 21, line 40, delete "540.5 (31.0)" and insert -- 341 (54.4) --, therefor.

In column 21, line 40, delete "341.5 (54.4)" and insert -- 54.1 (31.0) --, therefor.

In column 21, line 45, delete "Vd=CL/Ke" and insert -- $V_d=CL/K_e$ --, therefor.

In column 22, line 1, delete "AUC0-tau" and insert -- $AUC_{0-tau}$ --, therefor.

In column 22, line 42, delete "t1/2" and insert -- $t_{1/2}$ --, therefor.

In column 22, lines 46-47, delete "table below and illustrated in the table that follows." and insert -- table below. --, therefor.

In column 22, line 54, delete "Ke" and insert -- $K_e$ --, therefor.

In column 22, line 54, delete "Vd/F" and insert -- $V_d/F$ --, therefor.

In column 23, line 21, after "interchangeable" insert -- . --.